United States Patent [19]

Kulwiec et al.

[11] 4,412,824
[45] Nov. 1, 1983

[54] REMOVABLE PARTIAL DENTAL PROSTHESIS AND METHOD OF FORMING AND SUPPORTING THE SAME

[76] Inventors: Leonard J. Kulwiec, 9478 La Cuesta Dr., La Mesa, Calif. 92041; Michael F. X. Kulwiec, 2791 McBride, Unit No. 105, Santa Rosa, Calif. 95401

[21] Appl. No.: 303,560

[22] Filed: Sep. 18, 1981

[51] Int. Cl.³ .............................................. A61C 13/28
[52] U.S. Cl. .................................................... 433/170
[58] Field of Search ............... 433/178, 177, 172, 169, 433/170

[56] References Cited

U.S. PATENT DOCUMENTS 1,519,505 12/1924 Noyes ................................. 433/178
4,293,303 10/1981 Bona .................................... 433/177

*Primary Examiner*—Robert Peshock
*Attorney, Agent, or Firm*—Manfred M. Warren; Robert B. Chickering; Glen R. Grunewald

[57] ABSTRACT

A removable partial dental prosthesis is disclosed in which a universal, resiliently displaceable coupling is provided between the abutment tooth from which the prosthesis is stabilized and the base of the prosthesis which rests on the alveolar ridge. The coupling includes an arm cantilevered from an abutment tooth clasp and a resilient tubular member mounted to the arm and secured by a clip to the base. A method for support of the prosthesis in the mouth for limited displacement is disclosed as is a method to manufacture the prosthesis.

12 Claims, 9 Drawing Figures

U.S. Patent  Nov. 1, 1983  Sheet 1 of 2  4,412,824
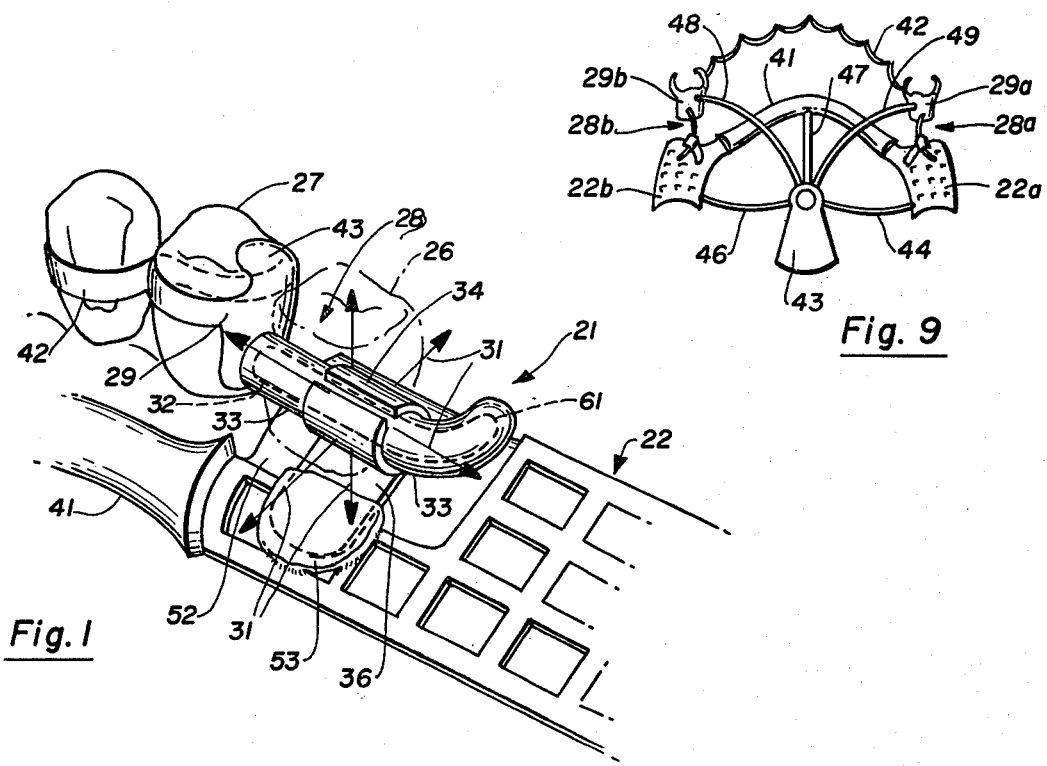
Fig. 9
Fig. 1
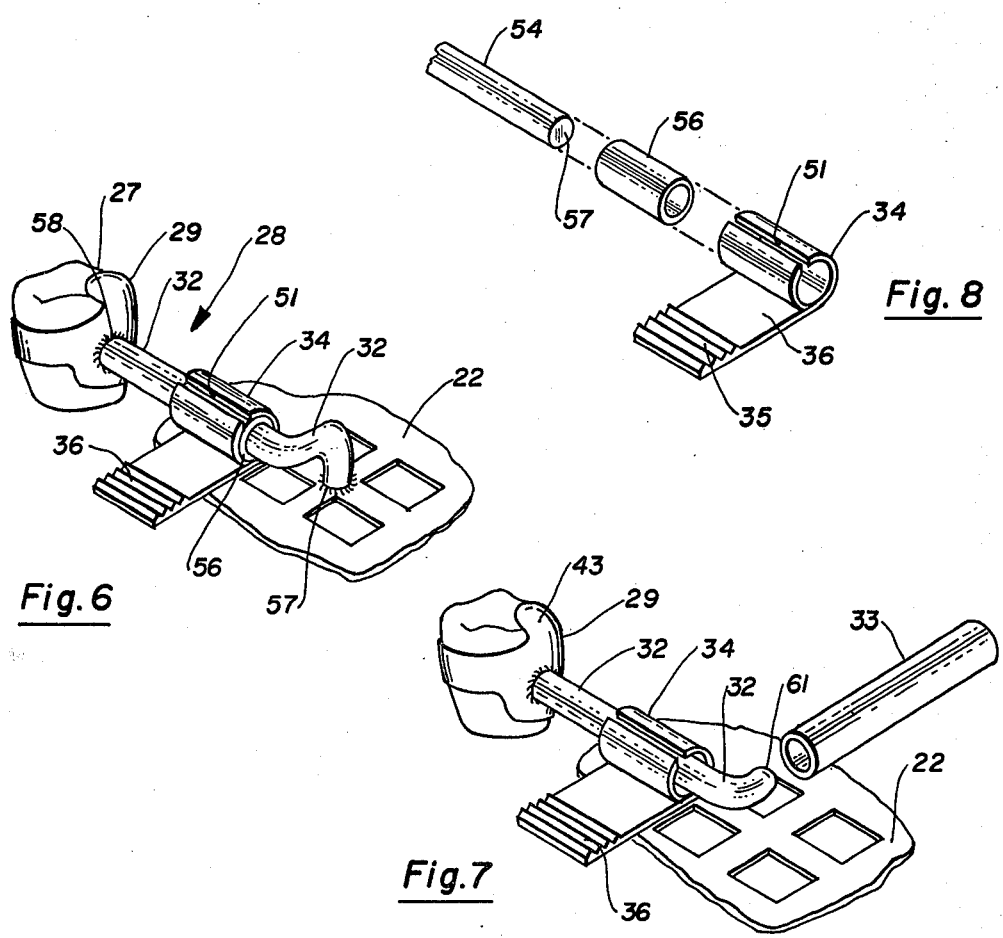
Fig. 6
Fig. 8
Fig. 7

REMOVABLE PARTIAL DENTAL PROSTHESIS AND METHOD OF FORMING AND SUPPORTING THE SAME

BACKGROUND OF THE INVENTION

Removable partial dental prostheses are employed to restore one or more, but not all, of the natural teeth of a patient. The primary objectives of a properly designed dental prosthesis include the preservation of remaining teeth, along with hard and soft oral tissue, the restoration of oral function, and the restoration of dental and facial aesthetics.

Removable partial dental prostheses are commonly formed with a base or saddle which rests on the oral mucosa in an edentulous space and is coupled by connector means to one or more abutment teeth, that is, a tooth which abuts or is adjacent to the edentulous space.

Perhaps one of the most common forms of partial dental prosthesis is the distal extension removable partial denture which is used to replace posterior teeth with artificial teeth on one or both sides of the mouth. Distal extensions are commonly secured to an abutment tooth by clasps, which are mounted on the abutment tooth to provide for stabilization and retention of the prosthesis, and a connector, which extends between the clasp and the base of the distal extension. The base or saddle of the distal extension rests on the alveolar ridge.

Since the mucosal covering over the alevolar bone can be compressed or displaced when loaded, for example, during mastication, a rigid connection between the abutment tooth clasp and the denture base results in substantial lateral loading of the abutment tooth. Thus, as the user of the denture chews a bolus of food, compression and resilient rebound of the mucosa on the alveolar ridge will cause the denture base to be vertically reciprocated, which reciprocation is in turn transferred to lateral displacement of the abutment tooth by the connection between the base and the clasp mounted on the abutment tooth.

Since natural teeth are supported by periodontal fibers which are well suited for support of compression loading but not well suited for repeated lateral displacement, the result of repeated lateral displacement is that the prosthesis gradually breaks down the periodontal fibers supporting the abutment tooth, with the further result that the abutment tooth and supporting bone are damaged. The abutment tooth will have to be removed and the denture supported from the next abutment tooth. Since the process repeats itself, there is a gradual breakdown of the natural teeth as a result of using a dental prosthesis which is rigidly secured to abutment teeth.

This problem is further exacerbated by the fact that during normal mastication, the loading forces are not simply in the vertical direction. During the chewing cycle the mandible moves diagonally downward and forward, then to the side that contains the bolus of food, then backwardly, and finally forward to complete the cycle. The chewing path, therefore, is eliptical, and the forces on any denture are multi-directional. Thus, the lateral or rocking force on the abutment tooth as a result of compression of the alveovar ridge mucosa by the dental prosthesis is also multi-directional, and the breakdown process of the periodontal membrane and fibers supporting the abutment tooth is accordingly more rapid than would be the case if the chewing action were merely vertical in direction.

Prosthodontists have long sought the most suitable design for distal extension removable partial dentures. Such designs require a balance between stress-free retention of the denture in the mouth and physiological integrity necessary for the reproduction of natural oral function. Dental journals have long reported the relatively high failure rate of distal extension partial dentures as a result of lateral stressing of abutment teeth, and great attention has been directed to the torque and stress forces applied to the abutment tooth and to the mucosa on the alveolar ridge, which also tends to become traumatized and destroyed through repeated compression.

In recent years attempts have been made to redirect and reduce the stress on the abutment tooth by providing a hinged connector between the abutment tooth and the base of the prosthesis. The proposed function of the hinge is to direct vertical force away from the abutment tooth and transfer that force to the alveolar ridge. Thus, a hinge connector in which the pivotal axis is horizontally oriented will permit downward displacement of the base without tilting or pulling the abutment tooth laterally to any substantial degree. Actually the hinge movement is arcuate and mastication, even in the vertical direction, can cause some rearward displacement of the abutment tooth.

The problem with hinged distal extension removable partials, however, is that the chewing action is not merely in the vertical direction, as above noted. Accordingly, the natural eliptical chewing action causes displacement of the prosthesis in directions which cannot be accommodated by a hinge connector with a horizontal axis. The abutment tooth, therefore, will still be rocked during mastication to such an excessive degree as to cause breakdown of the periodontal membrane. Moreover, it should be noted that lateral forces can be induced in directions which a hinge cannot accommodate by factors other than the normal eliptical chewing movement, such as off-center contact with the bolus of food, inaccurate set up of the artificial teeth, inaccurate bite registration, and natural occlusal diseases such as Bruxism.

The use of hinged removable partial denture prostheses, therefore, has been limited in nature, and the problems sought to be overcome by the structure still remain. The marginal improvement in dental performance of hinged partial prosthesis, therefore, has not justified the increased complexity of the prosthesis construction, and most prosthodontists still employ the rigidly connected distal extension removable partial denture.

OBJECTS OF THE INVENTION

Accordingly, it is an object of the present invention to provide a removable partial dental prosthesis which is capable of restoring oral function and dental and facial aesthetics without destruction of adjacent teeth and soft oral tissue.

Another object of the present invention is to provide a method of supporting a removable partial dental prosthesis in the mouth and particularly on the alveolar ridge which greatly reduces stress on the ridge and abutment teeth.

Still a further object of the present invention is to provide a method for the manufacture or formation of removable partial dentures which is adaptable to standard denture manufacturing techniques and yet includes structure providing enhanced performance of the prosthesis.

Another object of the present invention is to provide a method for supporting a dental prosthesis which enhances the life of the remaining teeth in the mouth and which does not afford a habitat for decay and infection causing debris.

It is also an object of the present invention to provide a dental prosthesis which is compact, relatively easy to manufacture, highly durable, and distributes and redirects localized stress forces.

The removable dental prosthesis and method of the present invention have other objects and features of advantage which will become more apparent from and are set forth in the following description of the preferred embodiment and the accompanying drawings.

SUMMARY OF THE INVENTION

The removable partial dental prosthesis of the present invention includes base means formed to mate with the oral mucosa for support of the prosthesis thereon, at least one artificial tooth mounted to the base, and connector means formed to couple the base to an abutment tooth. The improvement in the dental prosthesis is comprised, briefly, of the connector means being formed to couple the base means to the abutment tooth for limited universal displacement, that is, displacement along one or more of three mutually perpendicular axes. Additionally, the connector is preferably formed for resilient displacement with respect to the abutment tooth so as to resume a neutral position after displacement. In the preferred form a cantilevered arm surrounded by a resiliently compressible tube is held by a clip to provide the coupling between the base and tooth so as to insulate or reduce the stress on the abutment tooth from displacement of the prosthesis in any direction.

In a second aspect the method of the present invention includes the steps of removably supporting this prosthesis on the oral mucosa and coupling the base to the abutment tooth, with the improvement comprising accomplishing the coupling step by connecting the base to the abutment tooth for limited universal displacement.

In a third aspect of the present invention a method for forming a removable partial dental prosthesis is provided in which the improved method includes a step of mounting a resilient element between the abutment tooth and the base of the dental prosthesis so as to provide a universally displaceable coupling therebetween.

DESCRIPTION OF THE DRAWING

FIG. 1 is a fragmentary top perspective view of a removable partial dental prosthesis constructed in accordance with the present invention.

FIG. 6 is a top perspective view corresponding to FIG. 1 of an interim fabrication step for the fabrication of the dental prosthesis of the present invention.

FIG. 7 is a fragmentary top perspective view corresponding to FIG. 6 showing the next step in the fabrication of the dental prosthesis of the present invention.

FIG. 8 is an exploded top perspective view of the coupling assembly used in the dental prosthesis of the present invention.

FIG. 9 is a rear perspective view of a bilateral dental prosthesis showing the casting sprue and metallic parts which result after lost-wax investment casting.

DESCRIPTION OF THE PREFERRED EMBODIMENT

Figure 2:
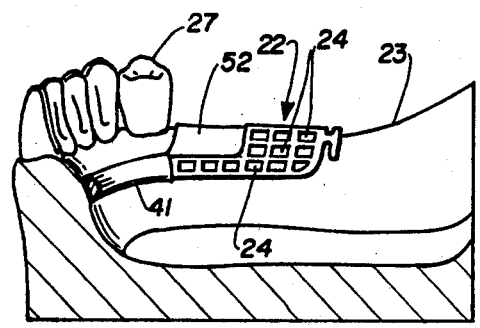
FIG. 2 is a side elevational view, in cross-section, of a mandible having the base portion of the prosthesis of FIG. 1 mounted thereon.
Figure 3:
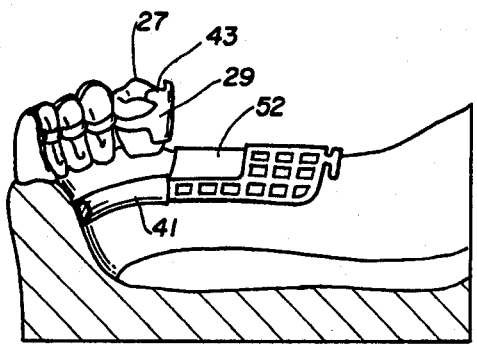
FIG. 3 is a side elevational view, in cross-section, showing a base portion and a clasp mounted on the abutment tooth.
Figure 4:
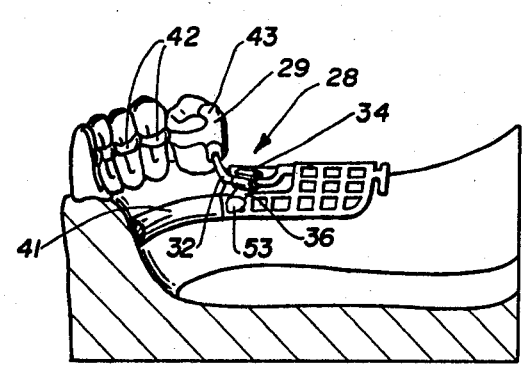
FIG. 4 is a side elevational view, in cross-section, showing a connector between the clasp and base portion.
Figure 5:
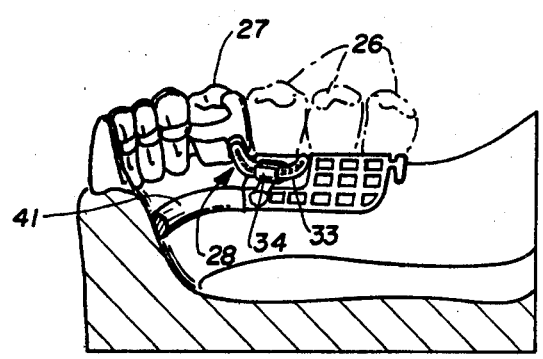
FIG. 5 is a side elevational view, in cross-section, showing the complete prosthetic assembly with artificial teeth shown in phantom.

Referring now to FIGS. 1-5, the removable partial dental prosthesis, generally designated 21, of the present invention can be seen to include base means 22 formed to mate with oral mucosa on alveolar ridge 23 for support of the prosthesis on the ridge. Base 22 has a saddle-like, generally U-shaped, cross-section which mates with ridge 23 and extends along the ridge in the edentulous space. The removable dental prosthesis illustrated herein is a distal extension of free-end of Kennedy Class I denture for replacement of lower posterior teeth. It will be understood, however, that the prosthesis of the present invention has application to other forms of removable dentures.

In the preferred form base 22 is formed of a dental metallic alloy that is compatible with and inert in the mouth and is here shown formed with a plurality of openings 24. These openings act as recesses which will allow interlocking of a plastic resin to the metallic base for support of artificial teeth 26 on the base. As will be understood, it is possible to provide a plurality of protrusions on base 22 for interlocking and securement of the plastic resin by which artificial teeth are mounted to the metallic base.

In order to secure the prosthesis on the alveolar ridge, connector means, generally designated 28, is provided and formed to couple base 22 to the natural tooth 27 abutting the edentulous space. Connector means 28 preferably includes clasp means 29 which has been molded so that it will slidably mount down over abutment tooth 27 and can accordingly be removed upwardly therefrom. Similarly, base 22 can be lifted upwardly off alveolar ridge 23. Thus, the assembly of the base and connector provide a dental prosthesis which can be removed from the mouth at the option and selection of the user.

As thus far described, the removable partial dental prosthesis of the present invention has elements which are commonly found in prior art partial dentures. Accordingly, such elements in combination do not, per se, constitute or comprise the present invention.

In the improved dental prosthesis of the present invention connector means 28 between base 22 and abutment tooth 27 is formed to couple the base to the abutment tooth for universal displacement, that is, displacement along any or all of three mutually perpendicular axes as indicated by arrows 31 in FIG. 1. Thus, instead of rigidly coupling base 22 to abutment tooth 27 or even hingedly coupling base 22 to abutment tooth 27, the connector means 28 of the dental prosthesis of the present invention provides a universally displaceable coupling between the abutment tooth and the base. This permits limited displacement of the base in any direction without a corresponding and equal direct transfer of the displacement of the abutment tooth. The universally displaceable coupling tends to isolate the abutment tooth from displacements of the prosthesis so that periodontal fibers supporting the abutment tooth are subjected to less stress.

In prior hinged partial dental prostheses the orientation of the axis of the hinge relieved stress on the abutment tooth in only one direction whereas the universal coupling of the prosthesis of the present invention relieves stress in all directions.

Moreover, hinged prostheses had the further disadvantage of gradually permanently compressing the mucosa on alveolar ridge 23 after repeated use. It is an important feature of the present invention that coupling 28 be formed so as to resiliently couple base 22 to abutment tooth 27. Such resilient coupling will be described in more detail, but it provides a base which will return to a neutral position and accordingly spring back away from the alveolar ridge to a neutral position when the loading force on the prosthesis is removed. Instead of permanently compressing the mucosa on the alveolar ridge, therefore, the resilient coupling of base 22 to tooth 27 assists in rebound of the base to a position which minimizes the duration of compression and allows recovery of the mucosa rather than gradual fatiguing and permanent traumatizing and compression of the mucosa and destruction of the underlying bone.

The details of construction of the preferred embodiment of the universally, resiliently displaceable dental prosthesis connector of the present invention can now be set forth. In the preferred form, removable clasp 29 has an arm 32 cantilevered therefrom. Arm 32 preferably is integrally cast with clasp 29 in the manner which will be more fully described hereinafter. A resiliently compressible element, preferably in the form of a tube 33 is mounted on arm 32 and interposed between base 22 and abutment 27. The coupling means of the present invention further includes a connector clip 34 having a tang portion 36 that is rigidly mounted to base 22, again during casting of the base as will be more fully described. Clip 34 extends around and grippingly engages resilient tubular element 33, as mounted on arm 32.

Accordingly, the combination of cantilevered mounting of arm 32 and the resiliency of member 33 provides a flexible connection between clasp 29 on the abutment tooth and base 32. Arm 32 will flex in either the horizontal or vertical directions, with resilient tube 33 also enabling compression in these directions, and the resilient tube 33 will enable axial compression along the central longitudinal axis of arm 32. The resiliency of flexible tube 33, therefore, enables at least limited deflection and displacement of the base member in any direction, and the cantilevering of the arm allows flexible distortion in directions transverse to the longitudinal axis of the arm.

As will be appreciated, it is possible to reverse the components comprising the coupling means of the present invention. Thus, arm 32 could be cantilevered from base 22 and clip 34 mounted to clasp 29. Since there is somewhat more room on the base than the clasp, however, it is preferable that the assembly be formed with the clip mounted to the base, rather than to the clasp.

As thus far described, the dental prosthesis of the present invention acts as a distal extension on one side of the mouth of the user. It is quite common, however, that a dental prosthesis will be required for both sides of the mouth of the user. Thus, as shown in FIG. 9, a pair of base portions or members 22a and 22b can be provided, as well as a pair of clasps 29a and 29b. Interconnecting the clasps and base members will be coupling means 28a and 28b, constructed in accordance with the present invention, as above described. Thus, universal resilient connections between the prosthesis and the abutment teeth to which they are mounted will be provided. As also will be understood, the prosthesis of the present invention is suitable for use in the upper jaw, as well as the mandible.

As will be appreciated, the flexible link or universal coupling means of the dental prosthesis of the present invention enables displacement in any direction, but forces displacing the prosthesis are transmitted through even the flexible coupling to abutment tooth 27. The effect of the flexible linkage is to reduce the transfer of forces, enable the alveolar ridge to absorb more force and to generally reduce localized stressing. When a bilateral dental prosthesis is used, such as shown in FIG. 9, it is a further important feature of the present invention to provide connector means 41 extending between and coupling base members or portions 22a and 22b for the transmission and support of loading forces from one side of the mouth to the other. Thus, deflections on one side during mastication will be supported by the base member on that side and will be transmitted for support by the base member on the opposite side through connector or bar 41. As will be described hereinafter, it is preferable that a lingual or palatal bar 41 be integrally cast with each of the base members for simplicity of construction and to insure significant transmittal and disbursement of loading forces to the opposite side of the mouth.

Formation of the removable partial dental prosthesis of the present invention can readily be accomplished through the use of conventional lost-wax investment casting techniques. Since the details of lost-wax investment casting are well known in the art, they will not be repeated in detail herein. Suffice it to say that after a master reproduction of the dental arch is made in dental stone of the individual's mouth, one or more base members 22 can be cast to mate with the oral mucosa of each of the alveolar ridges. Similarly, the clasps 29 and interconnecting links 42 can be molded to mate with the remaining natural teeth. Downward displacement of clasp 29 is limited by a rest portion 43 which engages the occlusal or incisal surface of abutment tooth 27.

As would also be well understood by one skilled in the art, lingual bar 41 can be cast integrally with base members 22a and 22b simply by using appropriating spruing and venting. As shown in FIG. 9, central sprue 43 is provided with channels 44 and 46 to the opposed base members or portions and a channel 47 which extends to lingual bar 41. Additionally a pair of flow channels 48 and 49 extend to the opposite clasps, with the lingual links 42 being cast integrally with clasps 29a and 29b.

The formation of the flexible link or coupling between the base and clasp can be best understood by reference to FIGS. 1 and 6–8. More particularly, clip 34 is prefabricated out of a dental metal as a clip having serration 35 in tang 36 and a slot 51 which will enable adjustment of the internal diameter of the clip for gripping engagement of tubular member 33. During the casting process (usually centrifugal casting), therefore, serrated tang 36 of the clip can be waxed to the base portion, particularly at the flattened area 52, so that upon casting a blob of metal 53 will rigidly secure or mount the clip to base 22.

Formation of arm 32 as an integral cantilevered extension of clasp 29 can be advantageously accomplished by employing a fusable wire 54 (FIG. 8) which is waxed to clasp 29 and extends through a ceramic spacer 56 mounted in slotted clip 34. The distal end 57 of wire 54 is waxed to base member 22. Upon casting, the fusable wire material dissolves leaving a channel which is filled by dental metal upon casting of the clasp and base member. As will be seen in FIG. 6, therefore, arm 32 is integrally formed at one end 58 with clasp 29 and at the other end 57 with base member 22. Ceramic spacer 56 still remains in the assembly and prevents arm 32 from being cast to metallic clip 34.

Once casting is completed, the sprues can be removed and the dental alloy polished. The ceramic spacer 56, which is frangible, can be broken away leaving arm 32 in spaced concentric relationship to clip 34. The end of arm 32 is severed at 61 so as to be free of base 22. Resiliently compressible tubular member 33 can now be mounted on arm 32 so as to fill the space between the arm and the clip and provide the universally deflectable link or coupling assembly shown in FIG. 1. It is preferable to use a bonding agent as both a lubricant and a means of bonding tube 33 to arm 32 during the mounting process. Clip 34 can be spread slightly to facilitate mounting of tube 33 on arm 32 and retightened after mounting. Additionally, once tube 33 is mounted on arm 32, the end of the tube can be closed by and adhesive so as to prevent the entry of decay and infection causing debris into the end of the tube. The turn or bend at the distal end 61 of arm 32 provides a simple means for preventing axial displacement of the clip over the end of the arm, and end 61 can be bent inwardly or outwardly depending on the space available in the prosthesis assembly.

The final step in formation of the dental prosthesis of the present invention is to secure artificial teeth 26 to base 22. This can be done by using conventional techniques, with either plastic or procelain artificial teeth being secured by an acrylic resin over base 22 and flexible coupling means 28. As will be appreciated, one of the important features of the flexible coupling means of the dental prosthesis of the present invention is that it is compact enough to permit the mounting of artificial teeth on top of the flexible coupling without producing unnatural and stress-causing tooth height.

The prosthesis of the present invention can be formed with conventional dental materials. Thus the base, bar and clasps can be formed of the metal alloys such as chromium-cobalt-nickel, and the porcelain or plastic teeth can be secured to the metalic saddle base 22 by an acrylic resin. Resiliently compressible tube 33 can be advantageously formed from silicon tubing which is bonded to metalic arm 32 by a suitable vulcanizing silicone adhesive.

The removable partial dental prosthesis of the present invention is constructed so that: it can be easily removed from the mouth of the user, it rapidly returns to a neutral position in the mouth, it minimizes the stress on the mucosa supporting the prosthesis, it minimizes the transfer of loading forces to the abutment teeth, it is simple to fabricate, and it provides good aesthetics when needed.

What is claimed is:

1. A removable partial dental prosthesis including base means formed to mate with oral mucosa for support of said prosthesis thereon, at least one artificial tooth mounted to said base means, and connector means formed to resiliently couple said base means to an abutment tooth for limited displacement along three mutually perpendicular axes, wherein the improvement in said dental prosthesis is comprised of:
    said connector means is formed with:
        (i) an arm mounted to extend away from one of said abutment tooth and said base means,
        (ii) connector clip means mounted to a remainder of said abutment tooth and said base means, and
        (iii) a resiliently compressible element interposed between said arm and said clip means, said clip means securing said arm to said clip means with said compressible element therebetween.

2. The removable partial dental prosthesis as defined in claim 1 wherein,
    said compressible element is formed as a resiliently compressible tubular element mounted concentrically on said arm, and
    said arm is mounted to said abutment tooth and said clip means is mounted to said base means and extends around and grippingly engages said tubular element as mounted on said arm.

3. The removable partial dental prosthsis as defined in claim 2, and
    clasp means formed for removable engagement on and anchoring to said abutment tooth,
    said arm being cantilevered and extending from said clasp means.

4. A distal extension removable partial denture including a base member formed for mating support on the alveolar ridge of the mouth of the user, at least one artificial tooth carried by said base member, a clasp member mounted to an abutment tooth proximate said alveolar ridge, and a flexible link resiliently coupling said base member to said clasp member for limited universal displacement of said base member with respect to said clasp member, wherein the improvement in said partial denture comprises:
    said flexible link is formed as a metallic arm rigidly secured to said clasp member and cantilevered therefrom, and a resiliently compressible tubular member mounted on said arm, and
    said coupling means further includes a clip member rigidly secured to said base member and formed to and mounted in gripping engagement with said compressible tubular member.

5. The distal extension removable partial denture as defined in claim 4 wherein,
    said clip member is formed with a slotted sleeve portion which extends around and grips said compressible tubular member.

6. A method of forming a removable partial dental prosthesis having a link between an artificial tooth carrying base means and an abutment tooth anchoring clasp means including the steps of casting said base means and said clasp means from a dental metal and coupling said base member to said clasp member for relative movement therebetween and mounting a resiliently displaceable element between said clasp means and said base means, wherein the improvement in said method is comprised of the step of:
    at the time of said casting step, casting an arm portion from said dental metal to expand from one of said base means and said clasp means,
    securing clip means to a remainder of said base means and said clasp means, said clip means being formed to extend around and substantially encircle said arm means, and mounting said resiliently displaceable element between said arm portion and said clip means.

7. The method of forming a removable partial dental prosthesis as defined in claim 6 wherein,
said base means, clasp means and arm portion are cast together as a unit, and the additional step of:
severing said arm portion from one of said base means and said clasp means prior to said mounting step.

8. The method of forming a removable partial dental prosthesis as defined in claim 7 wherein,
said securing step is accomplished during casting step by casting said clip means to one of said base means and said clasp means by a dental metal.

9. The method of forming a removable partial dental prosthesis as defined in claim 8 wherein,
said arm portion is cast in spaced relationship to said clip means by a frangible spacer element, and the additional step of:
breaking and removing said frangible spacer element from between said arm portion and said clip means prior to said mounting step.

10. The method of forming a removable partial dental prosthesis as defined in claim 9 wherein,
said mounting step is accomplished by mounting a tubular resilient element over said arm portion and inside said clip means.

11. A removable partial dental prosthesis including base means formed to mate with oral mucosa for support of said prosthesis thereof, at least one artificial tooth mounted to said base means, and connector means formed to couple said base means to an abutment tooth for limited displacement along three mutually perpendicular axes, wherein the improvement in said dental prosthesis is comprised of:
said connector means is formed for both articulated and linear displacement of said base means along all three of said mutually perpendicular axes.

12. The dental prosthesis as defined in claim 11 wherein,
said connector means includes a resiliently compressible element formed and coupling said base means to said abutment tooth for both articulated and linear displacement of said base means along said three mutually perpendicular axes.

* * * * *

UNITED STATES PATENT AND TRADEMARK OFFICE
CERTIFICATE OF CORRECTION

PATENT NO. : 4,412,824

DATED : November 1, 1983

INVENTOR(S) : Leonard J. Kulwiec and Michael F.X. Kulwiec

It is certified that error appears in the above-identified patent and that said Letters Patent are hereby corrected as shown below:

Claim 6, Col. 8, line 63, delete "expand" and insert ---extend---;

Claim 11, Col. 10, line 8, delete "thereof" and insert

---thereon---.

Signed and Sealed this

Tenth Day of January 1984

[SEAL]

Attest:

GERALD J. MOSSINGHOFF

Attesting Officer — Commissioner of Patents and Trademarks